United States Patent Office

Plant Pat. 2,305
Patented Nov. 19, 1963

2,305
AZALEA PLANT

Hubert B. Lewis and Helen H. Lewis, both of 16562 E. Leffingwell Road, Whittier, Calif.

Filed Sept. 7, 1962, Ser. No. 222,247
1 Claim. (Cl. Plt.—56)

The present invention relates to a new and distinct variety of azalea plant which was originated by us by crossing the Belgian Indian variety known as "Brillanta Belgica" (unpatented) with the variety known as "Mme. Pericat" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which are aware:

(1) Fast, strong and upright habits of growth;

(2) Smooth and attractive foliage;

(3) A distinctive and attractive Carmine Rose general color tonality of the flowers which resemble tuberous begonia flowers; and (4) Good forcing qualities.

In comparison with its seed parent, our new variety differs therefrom in most every way, including the production of smoother and more attractive foliage, a faster growing habit, better forcing qualities and the production of flowers which are entirely different in shape and color from those of either parent. The new variety is also a stronger and more upright grower than its pollen parent. These factors of distinction represent a new and unusual combination in the azalea plant world.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Upright.
Habit: Upright; branching.
Rooting habit: Good.
Foliage:
*Size.*—Medium.
*Quantity.*—Normal.
*Color.*—New foliage: upper side—Spinach Green, Plate 0960; under side—Scheeles Green, Plate 860/1. Old foliage: upper side—Spinach Green, Plate 0960; under side—Spinach Green, Plate 0960/1.
*Shape.*—Oval.
*Texture.*—Upper side—medium smooth or slightly veined; nearly flat. Under side—veined, but not rough.
*Margin.*—Smooth; well shaped.
*Aspect.*—Good; well shaped.
*Disease resistance.*—Above average resistance to ordinary diseases to which azalea plants are normally subject, as determined by comparison with other varieties grown under the same cultural conditions at Whittier, California.

*Flowers*

Borne: 2 or 3 to stem; on short stems.
Blooming habit: Medium heavy.
Blooming season: Normally in spring, but can be brought into bloom at other times of the year with proper pruning; very suitable for forcing.
Quantity of bloom: Free, both outdoors and in greenhouse.
Continuity: From one season to intermittent. Lasting quality—long.
Petalage: 5 petals to each hose, with outer hose petals being shorter than those of inner hose petals, and inner hose petals being extended over outer hose petals.
*Color.*—Carmine Rose, Plate 621/2 at outer edge of outer petals, shading to Carmine Rose, Plate 621/3 toward center, and outer edge of center petals being Carmine Rose, Plate 621/1, shading to Carmine Rose, Plate 621/2 toward center; 2 top petals of each hose have dots of darker shading.
*Texture.*—Medium.
*Appearance.*—Inside—tufted center. Outside—slightly ruffled.
*Shape.*—Ovate; oblong.
*Arrangement.*—From semi-double to double hose in hose; petals of outer hose being shorter than and offset from those of inner hose; tufted center.
Bud: Color—Carmine Rose, Plate 621.

*Reproductive Organs*

*Stamens*: 4 or 5 in number on average; some attached to center petals. Color—white.
Pollen: Sparse. Color—white.
Styles: Well developed. Color—yellow.
Ovaries: Normal.

We claim:

A new and distinct variety of azelea plant, substantially as herein shown and described, characterized particularly as to novelty by the unique combination of fast, strong and upright habits of growth, smooth and attractive foliage, a distinctive and attractive Carmine Rose general color tonality of the flowers and their resemblance to tuberous begonia flowers, and good forcing qualities.

No references cited.

Nov. 19, 1963 H. B. LEWIS ETAL Plant Pat. 2,305
AZALEA PLANT
Filed Sept. 7, 1962 2 Sheets-Sheet 1
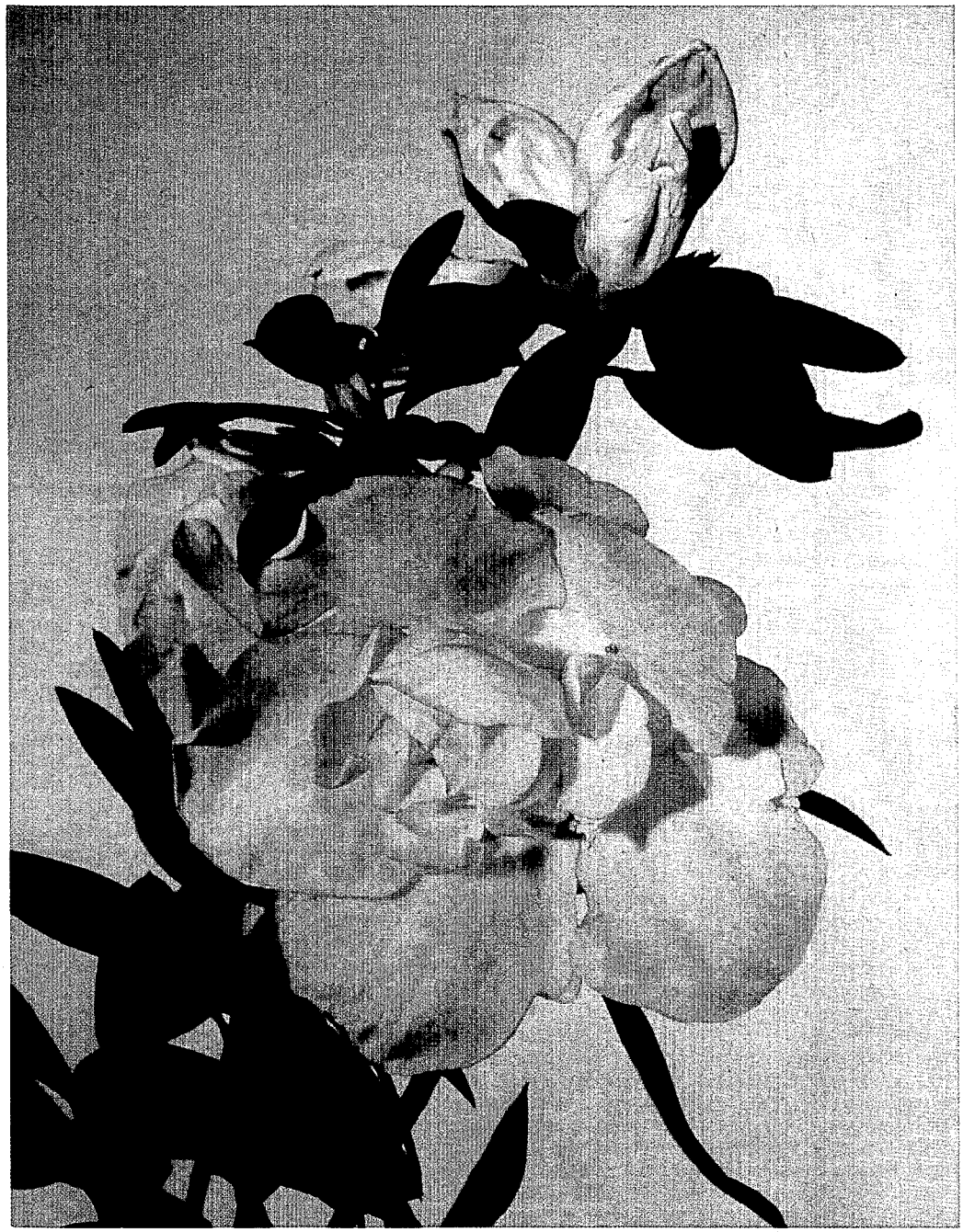
Inventors
H. B. Lewis and
H. H. Lewis
By: Robb & Robb
Attorneys.

AZALEA PLANT
Filed Sept. 7, 1962 2 Sheets-Sheet 2
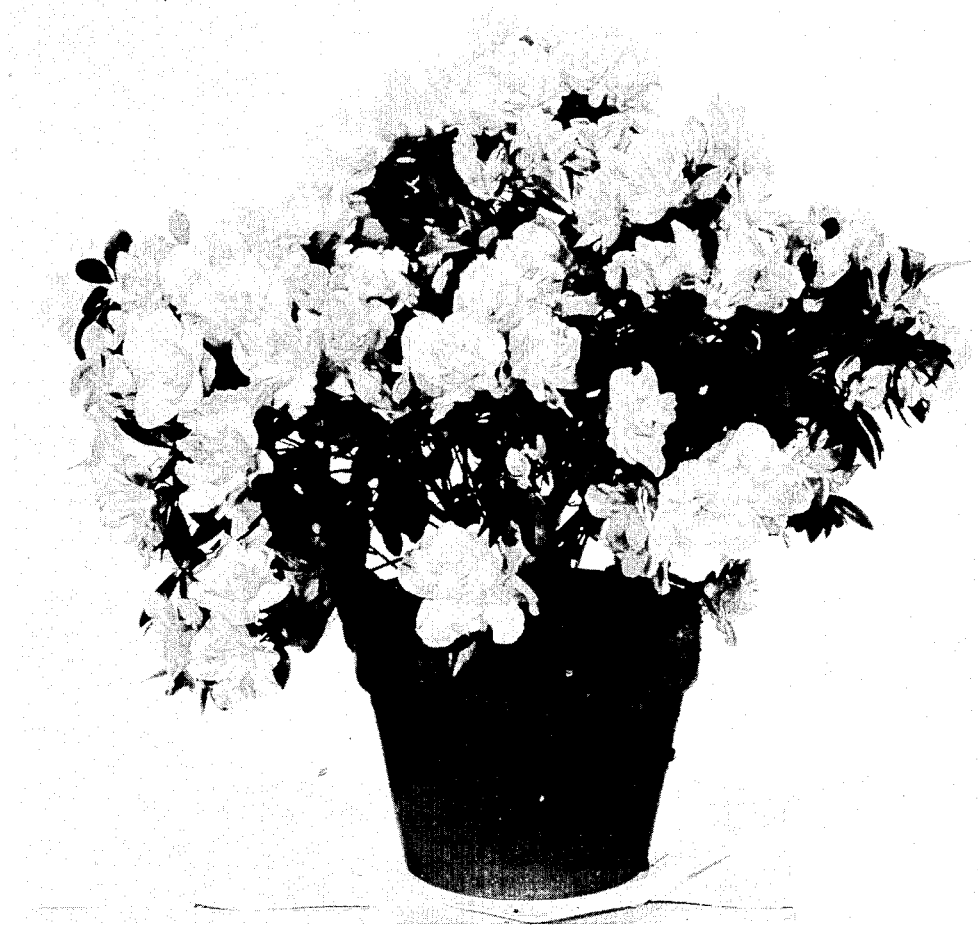
Inventors.
H. B. Lewis and
H. H. Lewis
By: Robb & Robb
Attorneys.